United States Patent [19]

Brochard et al.

[11] Patent Number: 4,720,565

[45] Date of Patent: Jan. 19, 1988

[54] PROCESS FOR PREPARING O-ALKYL S-(ALPHA-BRANCHED ALKYL) ALKYLPHOSPHONOTHIOATE

[75] Inventors: Jean-Michel Brochard, Alfortville, France; Stanley T. D. Gough, Essex, England

[73] Assignee: Rhone-Poulenc Agrochimie, Lyons, France

[21] Appl. No.: 770,214

[22] Filed: Aug. 28, 1985

[30] Foreign Application Priority Data

Sep. 14, 1984 [FR] France ................................. 84 14319

[51] Int. Cl.$^4$ ................................................. C07F 9/40
[52] U.S. Cl. ...................................................... 558/098
[58] Field of Search ............................................. 558/98

[56] References Cited

U.S. PATENT DOCUMENTS 3,751,529  8/1973  Baker et al. ............................. 558/98
3,838,180  9/1974  Randall et al. ......................... 558/98
4,305,891 12/1981  Jones ...................................... 558/98

Primary Examiner—Anton H. Sutto
Attorney, Agent, or Firm—Burns, Doane, Swecker & Mathis

[57] ABSTRACT

Process for preparing an O-alkyl S-(alpha-branched alkyl) alkylphosphonothioate of formula:

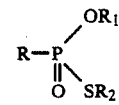

with R and $R_1$ = alkyl having 1 to 8 C.
$R_2$ = alpha-branched alkyl having 3 to 8 C.

It consists in reacting an O-(alkyl)alkylphosphonic acid halide with an alkyl mercaptan $HSR_2$ in an organic medium, in the presence of an acceptor for acid and a smaller amount of an auxiliary base.

Process useful for preparing insecticidal and nematocidal products.

12 Claims, No Drawings

PROCESS FOR PREPARING O-ALKYL S-(ALPHA-BRANCHED ALKYL) ALKYLPHOSPHONOTHIOATE

The present invention relates to a new process for preparing O-alkyl S-(alpha-branched alkyl)alkylphosphonothioates. Some of these compounds are known for their advantageous insecticidal and nematocidal properties, which can be used for crop protection.

It is known from U.S. Pat. No. 4,428,945 to prepare this type of compound by condensing an S-(tertiary alkyl)alkylphosphonothioic acid halide and an alcohol in the presence of a base.

This process is accomplished with a yield of approximately 70%, but enables the products in question to be obtained by means of an overall 4-stage process from a trialkyl phosphite.

The present invention has as its subject a new process for preparing these products which can be used at the final stage of an overall three-stage process, which is hence simplified and easier to carry out on the industrial scale.

The invention hence relates to a process for preparing an O-alkyl S-(alpha-branched alkyl)alkylphosphonothioate of formula:

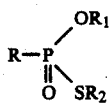

in which:
R is an alkyl group having from 1 to 8, and preferably from 1 to 4, carbon atoms,
$R_1$ is an alkyl group having from 1 to 8, and preferably from 1 to 4, carbon atoms,
$R_2$ is an alpha-branched alkyl group having from 3 to 8 carbon atoms, preferably 4 or 5 carbon atoms and preferably a tertiary alkyl group, wherein an O-(alkyl)alkylphosphonic acid halide is reacted with an (alpha-branched alkyl) mercaptan, according to the scheme:

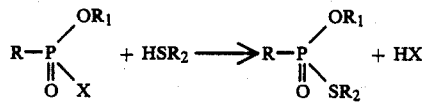

in which R, $R_1$ and $R_2$ have the significances given above and X is a halogen atom, preferably a chlorine or bromine atom, in an organic medium in the presence of an acceptor for acid and a smaller amount of an auxiliary base.

The reaction is advantageously performed at a temperature between 0° C. and 100° C. In general, a high temperature does not promote a good yield, and for this reason the reaction is preferably carried out at between 15° and 50° C., and for convenience at room temperature.

The acceptor for acid can be a strong organic base such as a tertiary amine, such as a trialkylamine, e.g. triethylamine or ethyldiisopropylamine or a pyridine such as pyridine and dimethylaminopyridine. This organic base is advantageously used in a substantially stoichiometric amount.

The acceptor for acid according to the invention must be mixed with a smaller amount of an auxiliary base.

The auxiliary base, mixed in the molar proportion of 0.5 to 15%, and preferably from 1 to 10%, is an organic base having a $pK_a$ at least equal to that of dimethylaminopyridine, and different from the first base. To this end, there can be used, in particular, a dialkyl- or alkyleneaminopyridine, the whole of the alkyl part containing from 1 to 6 carbon atoms, and especially 4-pyrrolidinopyridine and preferably 4-dimethylaminopyridine.

As suitable organic solvents, aliphatic hydrocarbons can be mentioned such as cyclohexane, optionally chlorinated hydrocarbons such as methylene chloride, ketones such as 2-butanone, and aromatic solvents such as benzene, toluene and xylene.

Preferably, and for convenience, the reaction is performed in an excess of the alkyl mercaptan used as reagent, and which acts in addition as a solvent.

The process according to the invention has the advantage of being able to give a substantial yield whereas, for this type of reaction, the prior results are poor and of no industrial value.

This reaction under good conditions furthermore opens the way to obtaining O-alkyl S-(alpha-branched alkyl)alkylphosphonothioates starting from a trialkyl phosphite according to a simplified three-stage process, the first two stages of which are known per se:

(1) Isomerization of a trialkyl phosphite to an O,O-dialkyl alkylphosphonate according to the scheme:

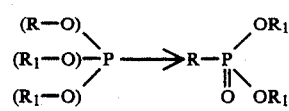

in which R and $R_1$, which may be identical or different, are an alkyl group having from 1 to 4 carbon atoms.

This reaction is performed, in a manner known per se, by heating the reactant to a temperature of 150° to 210° C. under nitrogen, in the presence of iodine or alkyl iodide.

(2) Halogenation of the O,O-dialkyl alkylphosphonate according to the scheme:

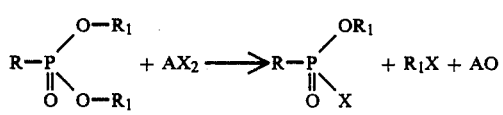

in which:
R and $R_1$ have the same significances as above,
$AX_2$ is a halogenating agent in which X denotes a halogen atom, preferably chlorine or bromine, and A an SO or CO group.

This reaction is performed at temperatures ranging from 40° to 150° C., in the presence of solvent and a catalyst, preferably a nitrogenous catalyst, e.g. a tertiary amine or an N,N-dialkylated amide (especially dimethylformamide), optionally under pressure.

(3) Condensation (reaction according to the invention)

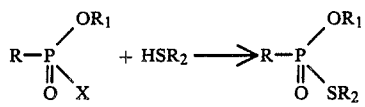

under the conditions described above.

This process has the advantage of giving the final products with a satisfactory overall yield on the industrial scale. In consequence, the use of the process according to the invention in this overall process also forms part of the invention.

The Examples which follow are given for guidance to illustrate the invention, but are not limitative.

EXAMPLE 1

Preparation of O-ethyl S-tert-butyl ethylphosphonothioate

In a 1-liter reactor, O-(ethyl)ethylphosphonothioc acid chloride (154.5 g; 1 mole) and dimethylaminopyridine (3.3 g; 0.03 mole) are poured in a single portion into tert-butyl mercaptan (270 g; 3 moles). Triethylamine (121.2 g; 1.2 mole) is then poured in slowly in the course of approximately 1 hour, while the mixture is cooled to a temperature between 0° and 20° C. When the addition is complete, the reaction mixture is maintained at approximately 20° C. for 4 hours with stirring. The reaction is then complete (yield greater than 95%).

The medium is washed with N hydrochloric acid (100 ml) and the aqueous phase is then decanted. The medium is then washed once again with water and the aqueous phase again decanted. The organic phase is then evaporated off under vacuum. O-Ethyl S-tert-butyl ethylphosphonothioate is obtained in 94% purity, and in a total yield of 80% in moles relative to the starting chloride.

The characterisation of the product obtained is performed by gas chromatography.

EXAMPLES 2 TO 4

By working as in Example 1, but replacing triethylamine by ethyldiisopropylamine and modifying the amount of catalyst (dimethylaminopyridine) and/or the temperature and/or the solvent, the same product is obtained under the conditions and with the results recorded in the Table below.

| No. | % in moles cata/reagent | Mole ratio amine/reagent | Tert-Bu SH mole ratio/reagent | Solvent | Temperature °C. | Reaction time in hours | Yield % in moles |
| --- | --- | --- | --- | --- | --- | --- | --- |
| 2 | 10 | 1 | 2 | $CH_2Cl_2$ | 22 | 72 | 84 |
| 3 | 1 | 1,1 | 2 | $CH_2Cl_2$ | 46 (reflux) | 6 | 70 |
| 4 | 3 | 2,2 | 2 | tert-$^1$Bu SH | 22 | 24 | 78 |

We claim:

1. A process for preparing an O-alkyl S-(alpha-branched alkyl)alkylphosphonothioate of formula:

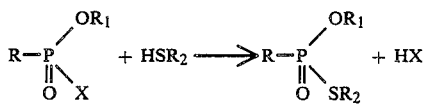

in which:
R is an alkyl group having from 1 to 8 carbon atoms,
$R_1$ is an alkyl group having 1 to 8 carbon atoms,
$R_2$ is an alpha-branched alkyl group having from 3 to 8 carbon atoms, wherein an O-(alkyl)alkylphosphonic acid halide is reacted with an (alpha-branched) alkyl mercaptan according to the scheme:

$$R-\underset{\underset{O}{\|}}{P}\underset{X}{\overset{OR_1}{\diagup}} + HSR_2 \longrightarrow R-\underset{\underset{O}{\|}}{P}\underset{SR_2}{\overset{OR_1}{\diagup}} + HX$$

in which R, $R_1$ and $R_2$ have the significances given above and X is a halogen atom, in an organic medium in the presence of an acceptor for acid and an auxiliary base, the auxiliary base being employed in a molar proportion of from about 0.5 to 15% based upon the halide reactant.

2. A process according to claim 1, wherein, in the reaction sheme, R and $R_1$ are each an alkyl group having from 1 to 4 carbon atoms.

3. A process according to claim 1, wherein $R_2$ is a tertiary alkyl group having 4 or 5 carbon atoms.

4. A process according to claim 1, wherein X is a chlorine atom.

5. A process according to one of claims 1 to 4, wherein the auxiliary base is a base different from the acceptor for acid.

6. A process according to one of claims 1 to 5, wherein the acceptor for acid is an organic base.

7. A process according to claim 6, wherein the acceptor for acid is triethylamine.

8. A process according to claim 5, wherein the auxiliary base is a dialkyl- or alkylene-4-aminopyridine derivative.

9. A process according to claim 8, wherein the auxiliary base is dimethylaminopyridine.

10. A process according to one of claims 1 to 9, wherein the auxiliary base is used in a molar proportion of from about 1 to 10%.

11. A process according to one of claims 1 to 10, wherein the reaction is performed in an organic solvent.

12. A process according to one of claims 1 to 11, wherein the reaction is performed in an excess of the reagent alkyl mercaptan.

* * * * *